United States Patent [19]

Kubo et al.

[11] Patent Number: 5,262,515

[45] Date of Patent: * Nov. 16, 1993

[54] CURABLE FLUORINE-CONTAINING POLYIMIDE

[75] Inventors: Motonobu Kubo; Tsutomu Kobayashi, both of Osaka, Japan

[73] Assignee: Daikin Industries, Ltd., Osaka, Japan

[*] Notice: The portion of the term of this patent subsequent to Aug. 7, 2007 has been disclaimed.

[21] Appl. No.: 550,493

[22] Filed: Jul. 10, 1990

Related U.S. Application Data

[63] Continuation-in-part of Ser. No. 363,718, Jun. 9, 1989, abandoned.

[30] Foreign Application Priority Data

Jun. 11, 1988 [JP] Japan .................. 63-144288

[51] Int. Cl.$^5$ .................. C08C 69/26; C08C 8/02; C08C 73/12
[52] U.S. Cl. .................. 528/353; 528/125; 528/128; 528/170; 528/172; 528/173; 528/174; 528/176; 528/185; 528/188; 528/220; 528/223; 528/229; 528/350; 528/352; 525/421; 525/426; 526/259; 526/260; 526/262; 526/263; 526/285
[58] Field of Search .................. 528/353, 125, 128, 170, 528/176, 172, 173, 179, 229, 220, 352, 188, 185, 223, 350; 525/421, 426; 526/263, 262, 260, 259, 285

[56] References Cited

U.S. PATENT DOCUMENTS

| | | | |
|---|---|---|---|
| 4,251,420 | 2/1981 | Antonoplos et al. | 528/352 |
| 4,299,750 | 11/1981 | Antonoplos et al. | 528/353 |
| 4,316,844 | 2/1982 | Waitkus et al. | 528/353 |
| 4,316,845 | 2/1982 | D'Alelio et al. | 528/352 |
| 4,321,198 | 3/1982 | D'Alelio et al. | 528/352 |
| 4,946,935 | 8/1990 | Ohsaka et al. | 528/353 |

FOREIGN PATENT DOCUMENTS 0032745 7/1981 European Pat. Off. .

OTHER PUBLICATIONS

Chemical Abstract 112: 57462n.
Chemical Abstract 112: 199238t.
Chemical Abstract 102: 62712s.
Chemical Abstract 77: 89197e.
Chemical Abstract 77: 88967u.
Chemical Abstract 112: 218329s.
Chemical Abstracts, vol. 106, No. 10, Mar. 9, 1987, p. 31. col. 1, Abstract No. 68089y, D. J. Capo et al.
Chemical Abstracts, vol. 102, No. 6, Feb. 11, 1985, p. 92, col. 1, Abstract No. 47500c, & JP-A-59 176321.

*Primary Examiner*—John Kight, III
*Assistant Examiner*—P. Hampton-Hightower
*Attorney, Agent, or Firm*—Birch, Stewart, Kolasch & Birch

[57] ABSTRACT

A curable fluorine-containing polyimide of the formula:

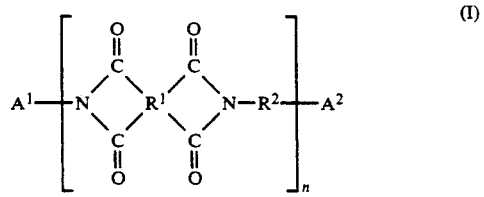

(I)

wherein $R^1$ is a group derived from an aromatic tetracarboxylic acid dianhydride by the removal of two acid anhydride groups, $R^2$ is a group derived from an aromatic diamine by the removal of two amino groups, $A^1$ is a residue of the formula:

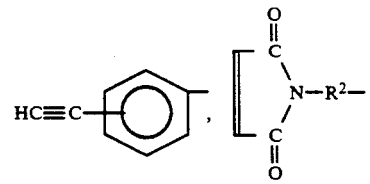

(Abstract continued on next page.)

ABSTRACT

-continued
or

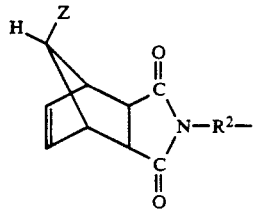

(wherein $R^2$ is the same as defined above, and Z is a hydrogen atom or an alkyl group having 1 to 5 carbon atoms), $A^2$ is a residue of the formula:

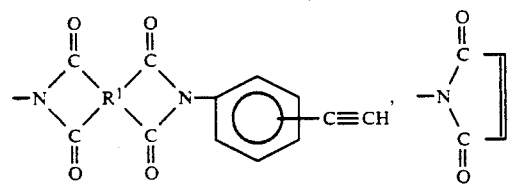

or

-continued

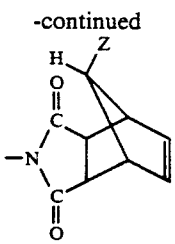

(wherein $R^1$ and Z are the same as defined above), and n is a number of 0 to 90, and at least one of the groups $R^1$ and $R^2$ in the formula (I) contains a substituted methylene group of the formula:

(wherein X is a residue of the formula):

wherein Rf is a perfluoroalkyl group having 1 to 10 carbon atoms, R'f is a perfluoroalkyl group having 1 to 12 carbon atoms, p is an integer of 1 to 3, q is an integer of 0 to 3, r is 0 or 1, s is an integer of 0 to 5 and t is an integer of 0 to 5, and Y is the same as X or a hydrogen atom, an alkyl group having to 8 carbon atoms or a fluoroalkyl group having 1 to 8 carbon atoms, provided that, when Y contains no fluorine atom, X contains at least 9 fluorine atoms, or when Y contains at least one fluorine atom, the total number of the fluorine atoms contained in X and Y is at least 8.

9 Claims, No Drawings

CURABLE FLUORINE-CONTAINING POLYIMIDE

This application is a continuation-in-part of application Ser. No. 07/363,718 filed on Jun. 9, 1989 now abandon.

BACKGROUND OF THE INVENTION

1. Field of the Invention

The present invention relates to a novel curable fluorine-containing polyimide which is useful for preparing a cured resin exhibiting high heat- and moisture-resistance and having a low refractive index and a low dielectric constant.

2. Description of the Related Art

The following compound, for example, has been known as a curable fluorine-containing polyimide having terminal unsaturated groups:

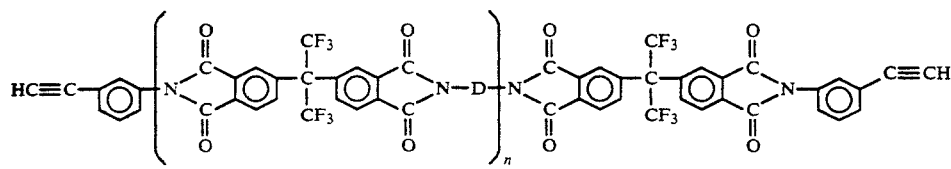

wherein D is a group derived from a diamine by the removal of two amino groups, and n is 1.0 on an average (cf. 18th International SAMPE Technical Conference, Oct. 7 to 9, 1986, pages 710 to 721).

A cured resin prepared from such a fluorine-containing polyimide may be unsatisfactorily applied on electronic or optical parts due to its inadequate moisture resistance, a high refractive index and a high dielectric constant.

SUMMARY OF THE INVENTION

An object of the present invention is to provide a curable fluorine-containing polyimide which is useful for preparing a cured resin having low moisture absorbance, high moisture resistance and also a low refractive index and a low dielectric constant.

The present invention provides a curable fluorine-containing polyimide of the formula:

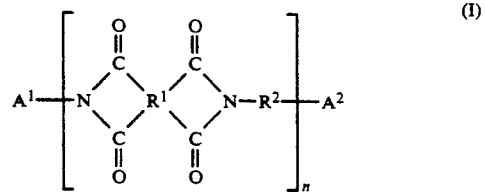 (I)

wherein $R^1$ is a group derived from an aromatic tetracarboxylic acid dianhydride by the removal of two acid anhydride groups, $R^2$ is a group derived from an aromatic diamine by the removal of two amino groups, $A^1$ is a residue of the formula:

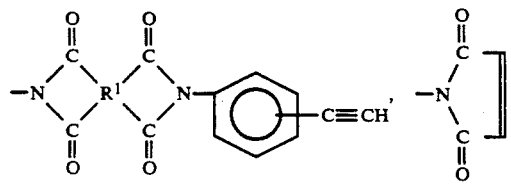

(wherein $R^2$ is the same as defined above, and Z is a hydrogen atom or an alkyl group having 1 to 5 carbon atoms), $A^2$ is a residue of the formula:

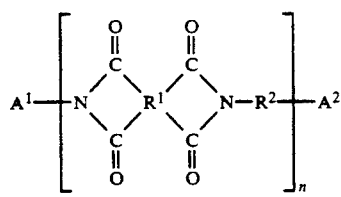

or

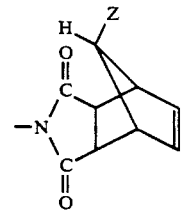

($R^1$ and Z are the same as defined above), and n is a number of 0 to 90, and at least one of the groups $R^1$ and $R^2$ in the formula (I) contains a substituted methylene group of the formula:

(wherein X is a residue of the formula):

$$-(CH_2)_p(CHF)_q(CFO)_r(CFCF_2O)_s(CF_2CF_2CF_2O)_tR'f$$
with Rf substituents wherein Rf is a perfluoroalkyl group having 1 to 10 carbon atoms, R'f is a perfluoroalkyl group having 1 to 12 carbon atoms, p is an integer of 1 to 3, q is an integer of 0 to 3, r is 0 or 1, s is an integer of 0 to 5 and t is an integer of 0 to 5; and Y is the same as X or a hydrogen atom, an alkyl group having 1 to 8 carbon atoms or a fluoroalkyl group having 1 to 8 carbon atoms, provided that, when Y contains no fluorine atom, X contains at least 9 fluorine atoms, or when Y contains at least one fluorine atom, the total number of the fluorine atoms contained in X and Y is at least 8.
DETAILED DESCRIPTION OF THE INVENTION
The present fluorine-containing polyimide includes the compounds of the following formulae:
wherein $R^1$, $R^2$, Z and n are the same as defined above.
Examples of the polyimide of the present invention are shown as follows:
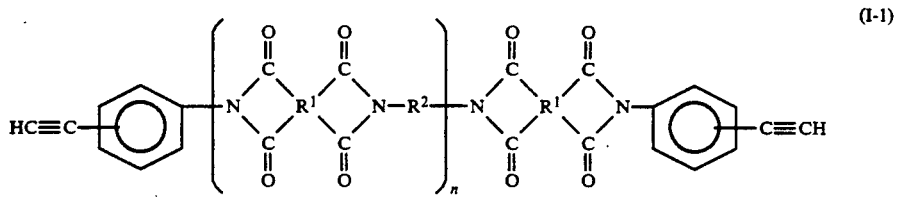
(I-1)
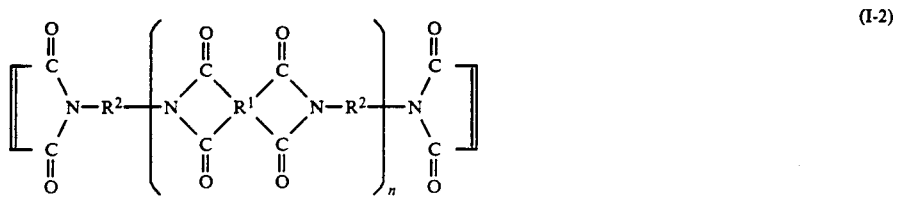
(I-2)
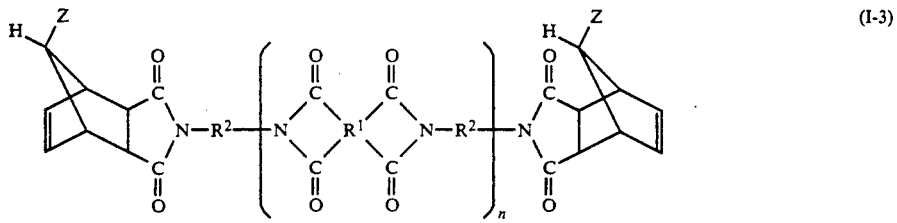
(I-3)
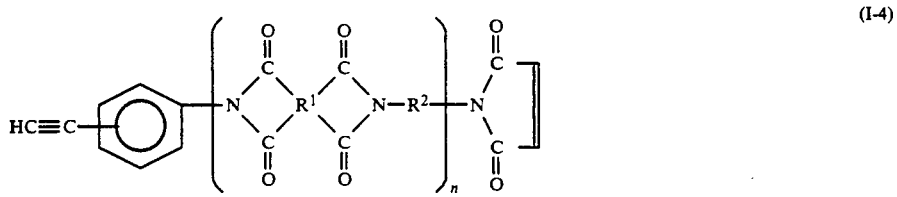
(I-4)
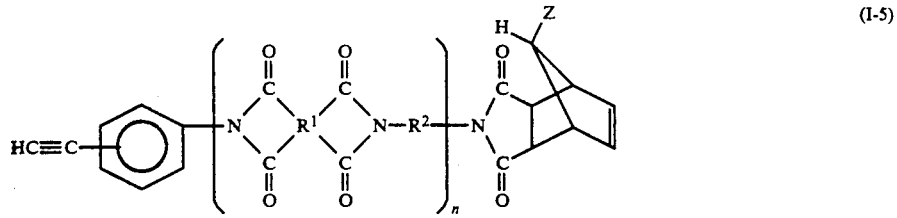
(I-5)
and
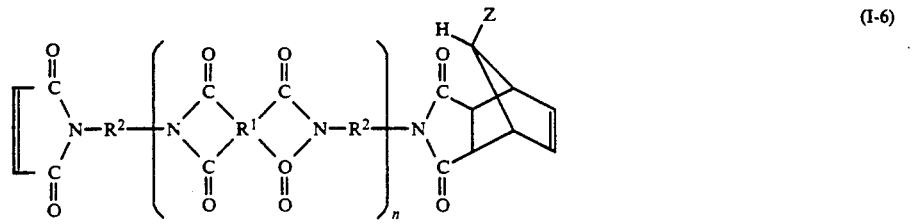
(I-6)

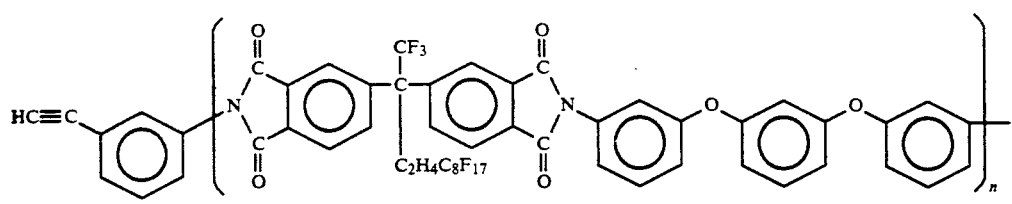
(1)
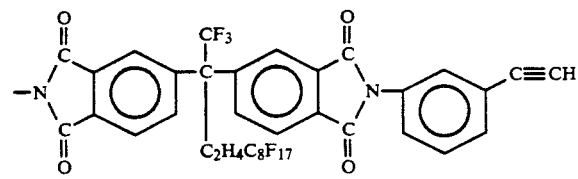
(2)
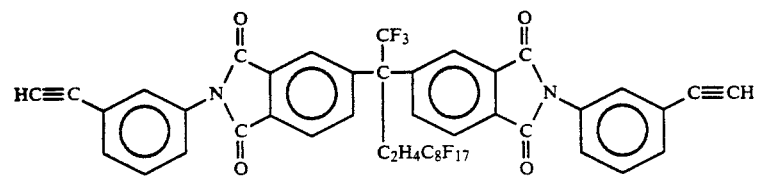
(3)
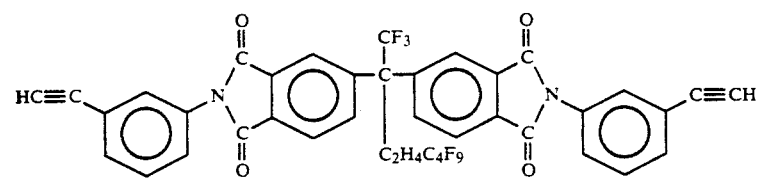
(4)
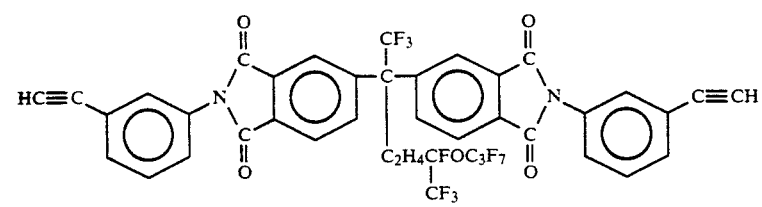
(5)
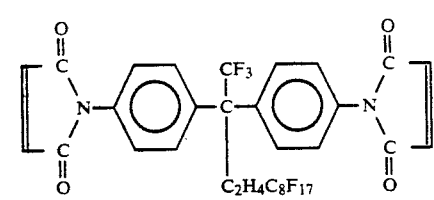
(6)
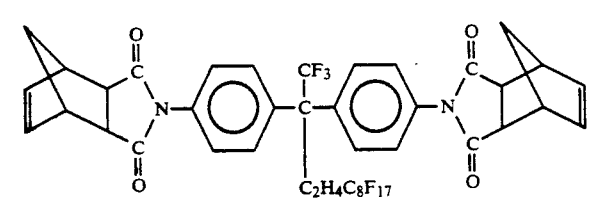
(7)
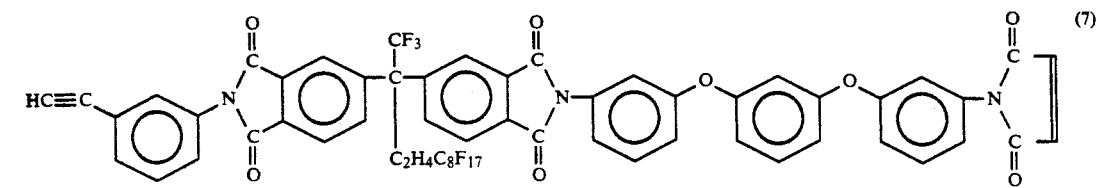
and

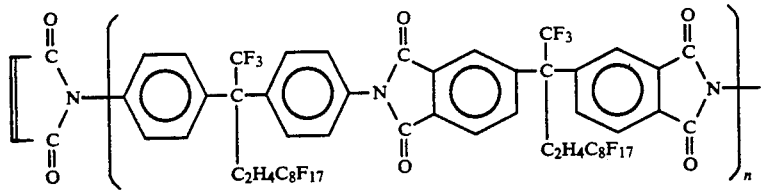

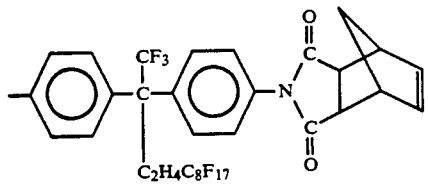

wherein n is the same as defined above.

The present fluorine-containing polyimide has a substituted methylene group of the following formula between aromatic rings in the repeating unit:

wherein X and Y are the same as defined above.

When n is 0 in the formula (I), the substituted methylene group should be contained in $R^1$ in the formula (I-1) and in $R^2$ in the formulae (I-2) and (I-3).

When n is not 0, at least one of the groups $R^1$ and $R^2$ in the main chain in the formula (I) should contain the substituted methylene group.

The groups $R^1$ and $R^2$ each containing the substituted methylene group can be represented as follows, respectively:

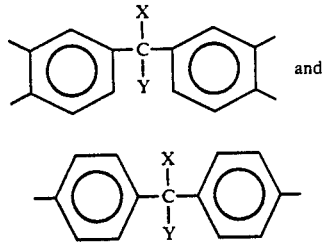

wherein X and Y are the same as defined above.

The present compound may have the following groups, for example, as $R^1$:

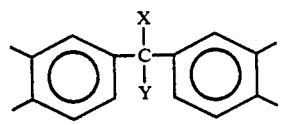

(wherein X and Y are the same as defined above),

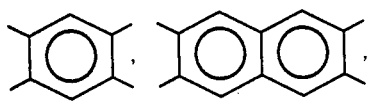

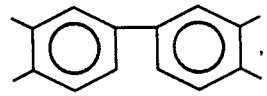

wherein $R^3$ is —O—, —CO—,

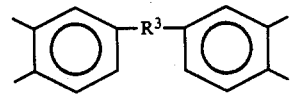

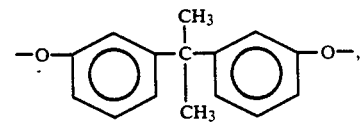

$-SO_2-$, 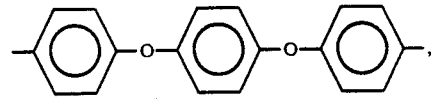, $-(CH_3)_2-$, $-C(CF_3)_2-$ or

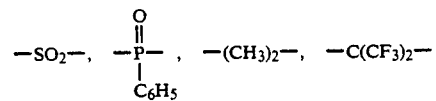

$-Si(CH_3)_2-]$,

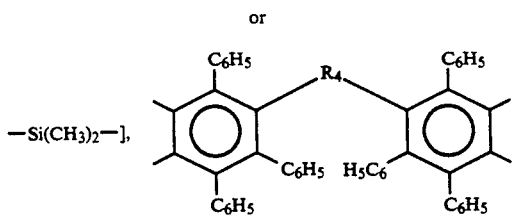

(wherein $R^4$ is $-C_6H_4-$, $-C_6H_4-O-C_6H_4-$ or $-C_6H_4-O-C_6H_4-O-C_6H_4-$), and

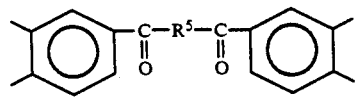

(wherein $R^5$ is —O—, —O—$(CH_2)_4$—O—, —O—$(CH_2)_6$—O—),

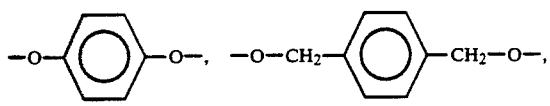

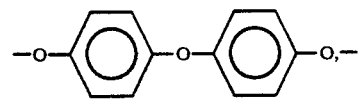

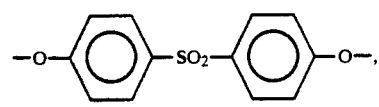

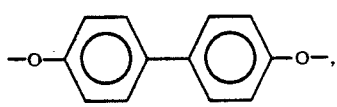

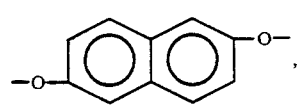

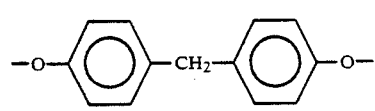

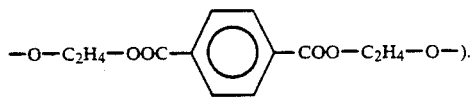

or

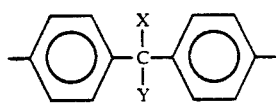

The following groups, for example, may be present as $R^2$:

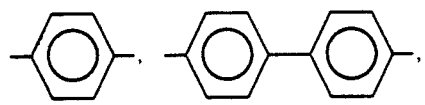

(wherein X and Y are the same as defined above),

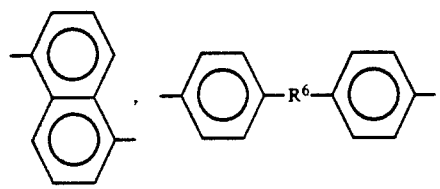

(wherein $R^6$ is —O—, —CO—, —S—, —CH$_2$—, —C(CH$_3$)$_2$—, —C(CF$_3$)$_2$—, —SO$_2$—,

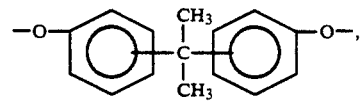

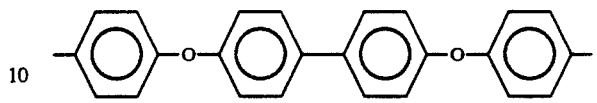

or

—Si(CH$_3$)$_2$—)

and

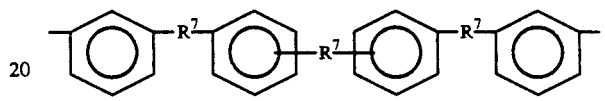

(wherein $R^7$ is —O—, —SO$_2$—, —CH$_2$—, —CO—, —C(CH$_3$)$_2$— or —S—).

In a preferred embodiment of the present invention, X in the substituted methylene group is a residue of the formula:

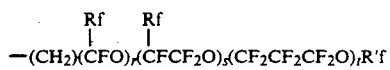

Rf, R'f, r, s and t are the same as defined above.

In another preferred embodiment of the present invention, X in the substituted methylene group is a residue of the formula:

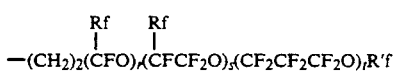

wherein Rf, R'f, r, s and t are the same as defined above.

In a further preferred embodiment of the present invention, X in the substituted methylene group is a residue of the formula:

wherein Rf, R'f, r and s are the same as defined above.

In a more preferred embodiment the present invention, X in the substituted methylene group is a residue of the formula:

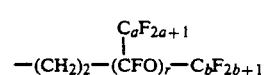

wherein r is the same as defined above, a is an integer of 1 to 8, and b is an integer of 1 to 8.

Y in the substituted methylene group is preferably an alkyl group having 1 to 8 carbon atoms such as a methyl group. More preferably, Y is a fluoroalkyl group having 1 to 8 carbon atoms such as a trifluoromethyl group.

The present compound (I-1) can be prepared according to the following reaction scheme:

When n is not 0:
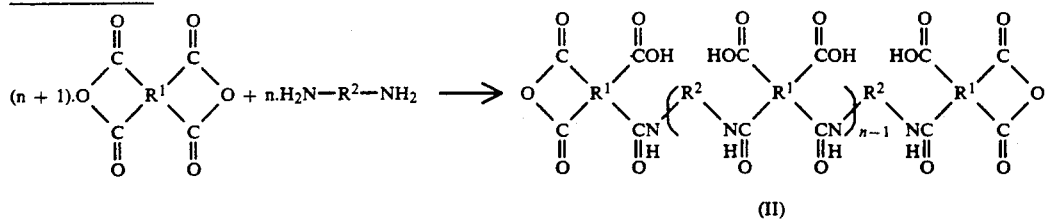
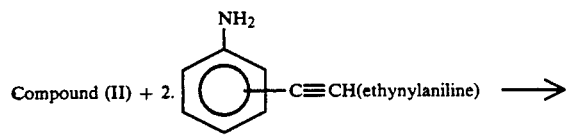
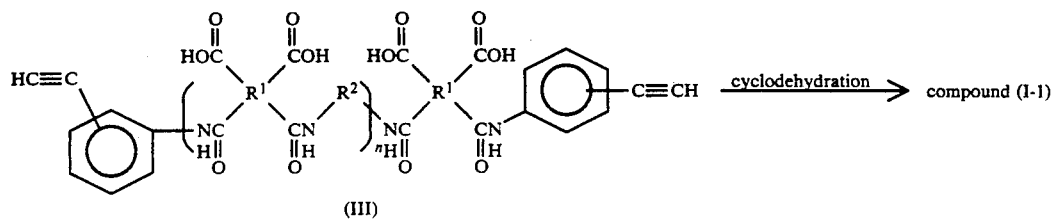
When n is 0:
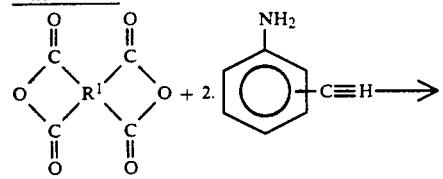
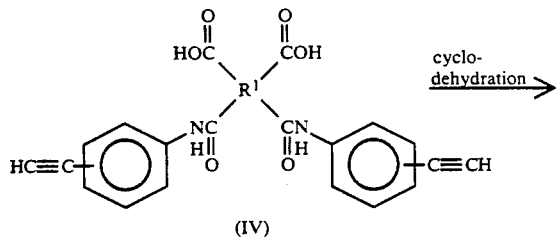
-continued
When n is 0:
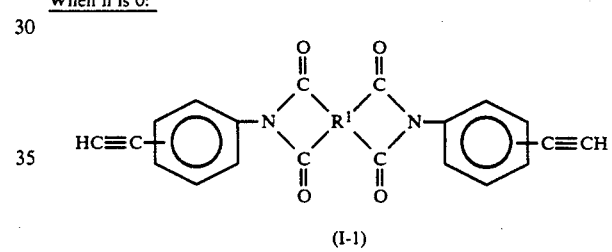
The present fluorine-containing polyimide compounds (I-2) and (I-3) can be prepared according to the following reaction scheme:
When n is not 0:
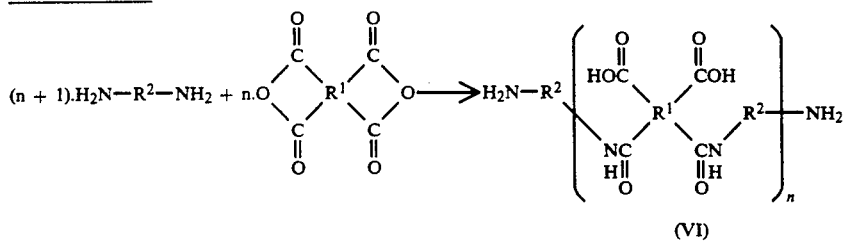
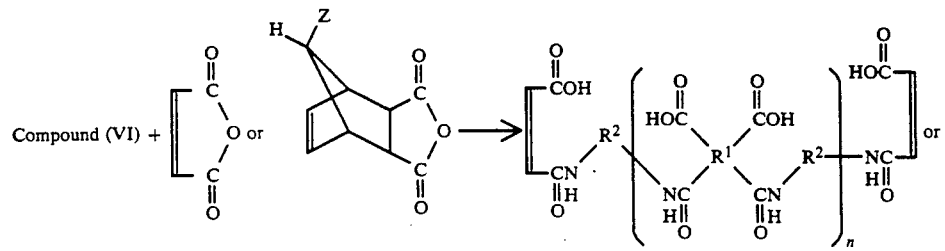

-continued
When n is not 0:
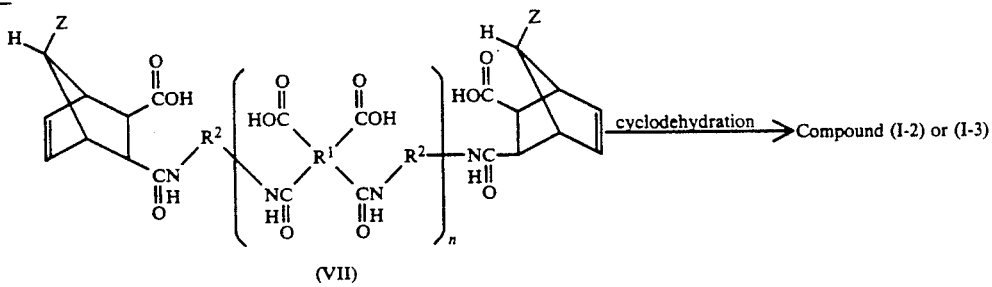
When n is 0:
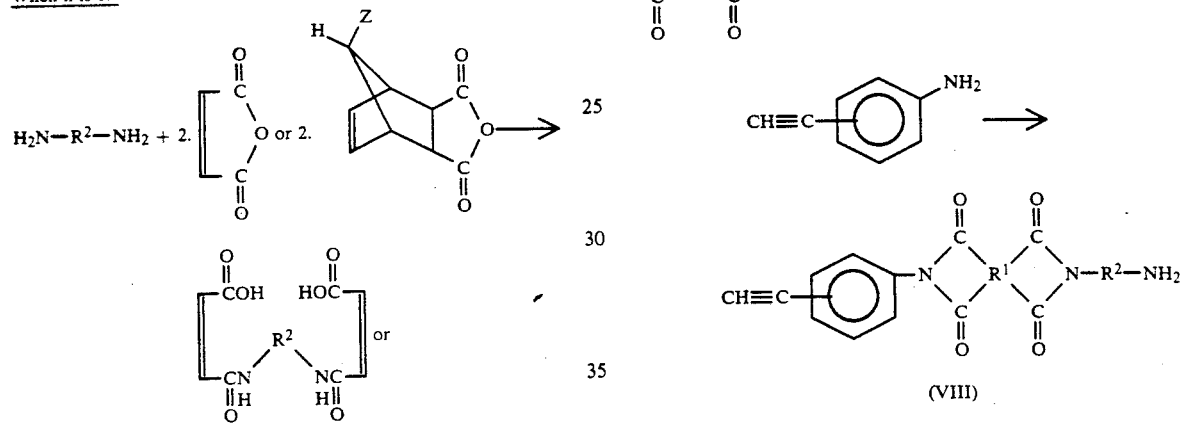
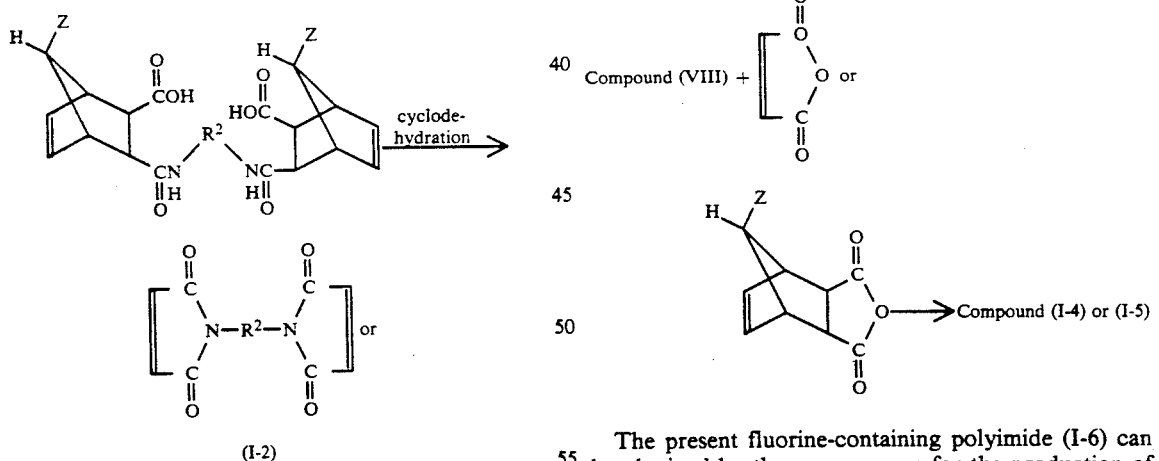
The present compounds (I-4) and (I-5), wherein n is 0, can be prepared as follows:
The present fluorine-containing polyimide (I-6) can be obtained by the same way as for the production of the compound (I-2), or (I-3) but that a mixture of
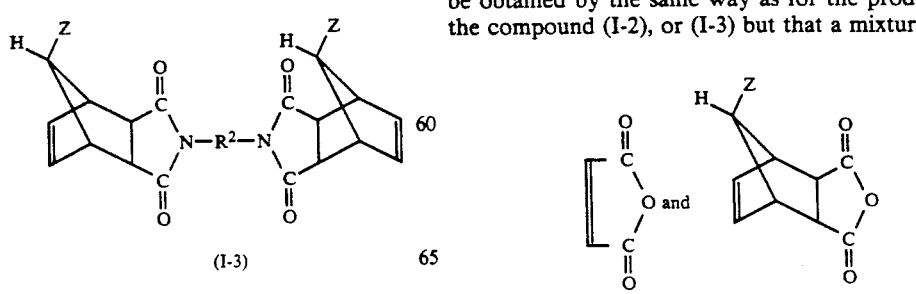
is used.

As shown in the reaction schemes, an amide acid is prepared as an intermediate. The reaction for the preparation of the amide acid is preferably carried out for 0.1 to 5 hours at a temperature in the range of from 0° to 15° C., in particular 20° to 100° C. in a solvent such as tetrahydrofuran, acetone, dioxane, N-methy-2-pyrrolidone, N,N-dimethylformamide, N,N-dimethylacetamide, dimethyl sulfoxide, diglyme, acetonitrile, 1,3-dimethyl-2-imidazolidinone or m-xylene hexafluoride with or without benzene, toluene or xylene.

Then, the amide acid is cyclodehydrated to form the present fluorine-containing polyimide. In this reaction, a dehydrating agent such as acetic anhydride, phosphorous pentoxide or conc. sulfuric acid is used. The reaction is preferably carried out in the presence of a catalyst and a base in a solvent. An oxide of an alkaline earth metal, or a carbonate, acetate, phosphate or sulfate of Fe(II) or (III), Ni(II), Mn(II) or (III), Cu(I) or (II) or Co(II) or (III) can be used as the catalyst. The base is, for example, trimethylamine, triethylamine, tributylamine or sodium acetate. The solvent previously used in the preparation of the amide acid is preferably used as such in this reaction. The dehydrating agent is usually used in a 1 to 20 times molar amount per mol of the amide acid. The catalyst and the base are added, based on the amount of the amide acid, in an amount in the range of from $1 \times 10^{-2}$ to $1 \times 10$ mol % and in an amount in the range of from 5 to 150 mol %, respectively. It is preferred to carry out the reaction for 2 to 24 hours at a temperature in the range of from 100° to 250° C., in particular from 120° to 280° C.

The present fluorine-containing polyimide compounds (I-1), (I-2) and (I-3) can be cured by heating at a temperature in the range of from 200° to 500° C., preferably from 250° to 400° C. for 0.1 to 5 hours. Prior to curing, a compound containing an ethynyl or ethylene group, such as an acrylic, styrene, vinylether or vinylester compound may be added to the present compound. To the present compounds (I-2) and (I-3), a diamine compound can also be added.

In addition, a filler may be added to the fluorine-containing polyimide. The filler used is, for example, calcium carbonate, silica, alumina, titania, aluminium hydroxide, aluminium silicate, zirconium silicate, zircon, glass, talc, mica, graphite, aluminium, copper or iron in a powder or short fibrous form.

The present fluorine-containing polyimide can be molded by, for example, compression or transfer molding. The molding may be easily carried out by the addition of the filler. It is also possible to coat the present compound as a varnish on a substrate.

The present fluorine-containing polyimide can be suitably used as a heat- and moisture-resistant material in, for example, a matrix resin for an aerospace structural material; a base resin for a heat resistant adhesive and a conductive adhesive; a rigid or flexible printed board material; a sealing agent for electric parts such as a semiconductor device; a passivation film; an interlayer insulating film; an α-ray blocking film; a protecting film on a surface against an external force; an insulating and reinforcing material for wire bonding parts; a masking material for ion implantation and lift-off; an oriented film for a liquid crystal display device; a sealing and protecting coating agent for optical parts such as a glass fiber and LED; and a protecting film for a solar battery.

PREFERRED EMBODIMENTS OF THE INVENTION

The invention is further illustrated by the following Examples.

EXAMPLE 1

To a stirred mixture of the compound (32.89 g; 0.04 mol) of the formula:

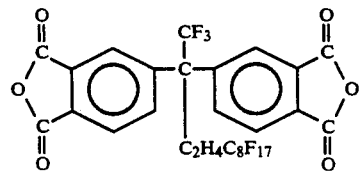

with N-methylpyrrolidone (NMP; 60 ml) in a 200 ml three necked flask, a solution of 1,3-bis(3-aminophenoxy)benzene (APB; 5.85 g; 0.02 mol) in NMP (15 ml) was slowly dropwise added at a room temperature. After stirring for one hour at 50° C., 3-aminophenylacetylene (APA; 5.04 g; 0.043 mol) in NMP (6 ml) was added and heated. Then, benzene was added and heated under reflux for 20 hours at 140° C. with removing water by a Dean-Stark condenser. The reaction solution was cooled to the room temperature and poured into ethyl alcohol to precipitate a reaction product. The reaction product was filtered and washed three times with ethyl alcohol to remove NMP. Then, ethyl alcohol was distilled off under a reduced pressure. After drying for 24 hours at 80° C. under a reduced pressure, the compound of the formula:

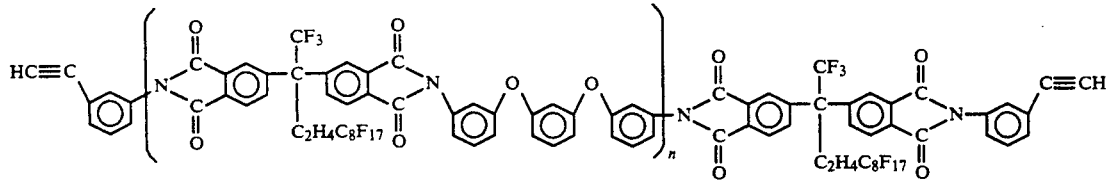

wherein n is 1.0 on an average,
was obtained. Yield: 32.43 g (0.015 mol; 77%). The value n was calculated by a quantitative analysis of terminal acetylene according to L. Barnes, Jr., Anal. Chem., 31 (3), (1959).

$^1$H-NMR (CDCl$_3$/TMS) δ [ppm]:8.1–6.7 (m, 32H), 3.11 (s, 2H), 3.0–1.6 (broad, 8H).

$^{19}$F-NMR (CDCl$_3$/TFA) δ [ppm]:–13.1 (s, 6F), 2.1 (t, 6F), 35.7 (broad, 4F), 43.0 (broad, 12F), 44.1 (broad, F), 47.3 (broad, 4F). IR, γ [cm$^{-1}$]:3300, 1780, 1725, 1585, 1480, 1430, 1375, 1240, 1200, 1170, 1140, 1100, 1010, 980, 910, 870, 840, 790, 740, 720, 710.

EXAMPLE 2

In a 200 ml three necked flask, a mixture of the compound (41.12 g; 0.05 mol) of the formula:

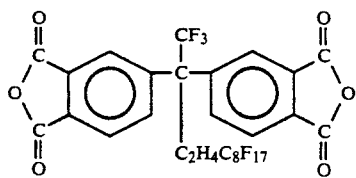

with APA (6.44 g; 0.055 mol) and NMP (70 ml) was stirred for one hour at 50° C. and then further heated. Then, to the mixture, toluene was added and heated under reflux for 15 hours at 140 ° C with removing water by a Dean-Stark condenser. The reaction solution was cooled to a room temperature and poured into ethyl alcohol to precipitate a reaction product. The reaction product was filtered and washed three times with ethyl alcohol to remove NMP. Then, ethyl alcohol was distilled off under a reduced pressure. After drying for 24 hours at 80° C. under a reduced pressure, the compound of the formula:

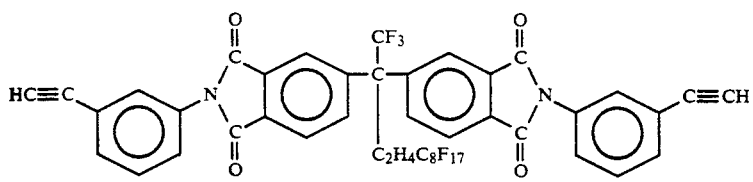

was obtained. Yield: 34.30 g (0.034 mol; 67%).

$^1$H-NMR (CDCl$_3$/TMS) δ [ppm]: 8.1-7.2 (m, 14H), 3.11 (s, 2H), 3.0-1.6 (broad, 4H).

$^{19}$F-NMR (CDCl$_3$/TFA) δ [ppm]:−13.1 (s, 3F), 2.1 (t, 3F), 35.8 (broad, 2F), 43.1 (broad, 6F), 44.0 (broad, F), 47.3 (broad, 2F).

IR, γ [cm$^{-1}$]:3300, 1780, 1720, 1600, 1580, 1480, 1430, 1370, 1230, 1200, 1170, 1140, 1100, 1005, 970, 785, 740, 710, 700.

EXAMPLE 3

In a 200 ml three necked flask, a mixture of the compound (43.56 g; 0.07 mol) of the formula:

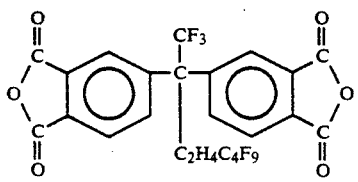

with APA (8.79 g; 0.075 mol) and NMP (80 ml) was stirred for one hour at 50° C. and then further heated. Then, to the mixture, toluene was added and heated under reflux for 20 hours at 140° C. with removing water by a Dean-Stark condenser. The reaction solution was cooled to a room temperature and poured into ethyl alcohol to precipitate a reaction product. The reaction product was filtered and washed three times with ethyl alcohol to remove NMP. Then, ethyl alcohol was distilled off under a reduced pressure. After drying for 24 hours at 80° C. under a reduced pressure, the compound of the formula:

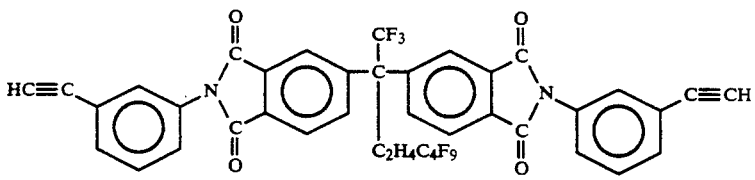

was obtained. Yield:41.33 g (0.050 mol; 72%).

$^1$H-NMR (CDCl$_3$/TMS) δ [ppm]:8.1-7.2 (m, 14H), 3.12 (s, 2H), 3.0-1.6 (broad, 4H).

$^{19}$F-NMR (CDCl$_3$/TFA) δ [ppm]:−13.3 (s, 3F), 2.3 (t, 3F), 35.2 (broad, 2F), 45.2 (broad, 2F), 47.3 (broad, 2F).

IR, γ [cm$^{-1}$]:3300, 1780, 1720, 1600, 1570, 1540, 1480, 1430, 1370, 1235, 1200, 1170, 1140, 1100, 1010, 970, 870, 790, 740, 710, 700.

EXAMPLE 4

In a 200 ml three necked flask, a mixture of the compound (41.30 g; 0.06 mol) of the formula:

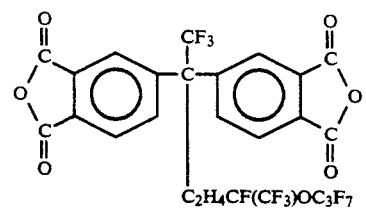

with APA (7.73 g; 0.066 mol) and NMP (70 ml) was stirred for one hour at 50° C. and then further heated. Then, to the mixture, toluene was added and heated under reflux for 15 hours at 140° C. with removing water by a Dean-Stark condenser. The reaction solution was cooled to a room temperature and poured into ethyl alcohol to precipitate a reaction product. The reaction product was filtered and washed three times with ethyl alcohol to remove NMP. Then, ethyl alcohol was distilled off under a reduced pressure. After drying for 24 hours at 80° C. under a reduced pressure, the compound of the formula:

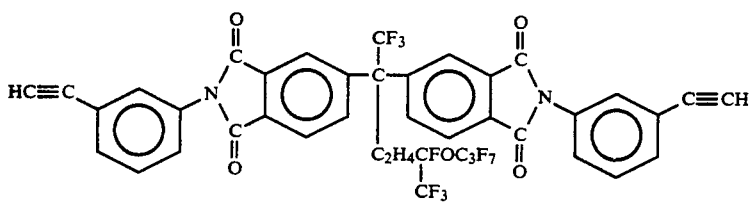

was obtained. Yield:39.69 g (0.045 mol; 75%).

$^1$H-NMR (CDCl$_3$/TMS) δ [ppm]:8.1–7.1 (m, 14H), 3.11 (s, 2H), 3.0–1.6 (broad, 4H).

$^{19}$F-NMR (CDCl$_3$/TMS) δ [ppm]:–12.2 (s, 3F), 2.9 (t, 3F), 3.1 (broad, 2F), 4.7 (d, 3F), 51.3 (broad, 1F), 52.8 (s, 2F). IR, γ [cm$^{-1}$]:3300, 1780, 1720, 1600, 1570, 1480, 1430, 1370, 1230, 1200, 1160, 1005, 970, 840, 750.

EXAMPLE 5

To a stirred mixture of the compound (35.62 g; 0.05 mol) of the formula:

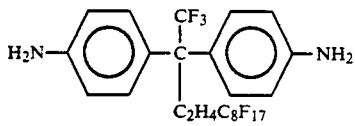

with m-xylene hexafluoride (m-XHF; 150 ml) in a 500 ml four necked frask, a solution of maleic anhydride (12.7 g; 0.13 mol) in m-XHF (150 ml) was slowly dropwise added at 50° C. and then stirred for 30 minutes at the same temperature. Then, benzyltrimethylammonium chloride (BTMAC; 0.5 g), Ni(OAc)$_2$.4H$_2$O (0.5 g) and conc. sulfuric acid (1.2 ml) were added to the reaction mixture and heated under reflux for 10 hours with removing water by a Dean-Stark condenser. An organic phase was neutralized with an aqueous Na$_2$CO$_3$ solution, washed two times with an aqueous NaCl solution and dried over anhydrous Na$_2$SO$_4$. Then, m-XHF was distilled off under a reduced pressure to obtain the compound of the formula:

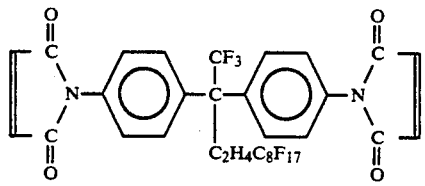

Yield:28.10 g (0.032 mol; 64%).

$^1$H-NMR (CDCl$_3$/TMS) δ [ppm]: 7.43 (s, 8H), 6.88 (s, 4H), 3.0–1.5 (broad, 4H).

$^{19}$F-NMR (CDCl$_3$/TFA) δ [ppm]:–12.8 (s, 3F), 2.2 (t, 3F), 35.9 (broad, 2F), 43.1 (broad, 6F), 43.7 (broad, F), 47.3 (broad, 2F).

IR, γ [cm$^{-1}$]:3500, 1720, 1610, 1520, 1400, 1380, 1200, 1140, 1060, 1020, 1000, 970, 950, 830, 700.

EXAMPLE 6

To a stirred mixture of the compound (35.62 g; 0.05 mol) of the formula:

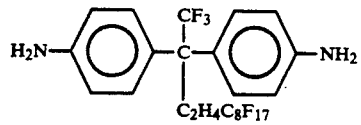

with m-XHF (150 ml) in a 500 ml four necked flask, a solution of 5-norbornene-2,3-dicarboxylic anhydride (21.3 g; 0.13 mol) in m-XHF was slowly dropwise added at 50° C. and then stirred for 30 minutes at the same temperature. Then, BTMAC (0.5 g), Ni(OAc)$_2$.4-H$_2$O (0.5 g) and conc. sulfuric acid (1.2 ml) were added to the reaction mixture and heated under reflux for 10 hours with removing water by a Dean-Stark condenser An organic phase was neutralized with an aqueous Na$_2$CO$_3$ solution, washed two times with an aqueous NaCl solution and dried over anhydrous Na$_2$SO$_4$. Then, m-XHF was distilled off under a reduced pressure to obtain the compound of the formula:

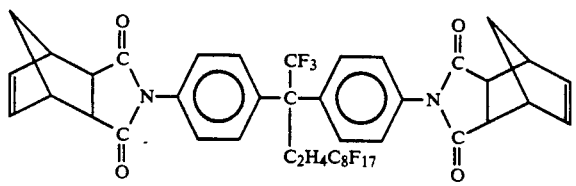

Yield:34.66 g (0.035 mol:69%).

$^1$H-NMR (CDCl$_3$/TMS) δ [ppm]:7.25 (q, 8H), 6.23 (s, 4H), 3.43 (m, 8H), 3.1–1.6 (broad, 4H), 1.7 (q, 4H).

$^{19}$F-NMR (CDCl$_3$/TFA) δ [ppm]:–13.0 (s, 3F), 2.2 (t, 3F), 35.8 (broad, 2F), 43.1 (broad, 6F), 44.0 (broad, F), 47.4 (broad, 2F).

IR, γ [cm$^{-1}$]:3400, 1710, 1510, 1375, 1200, 1170, 1140, 1000, 820, 720, 700.

EXAMPLE 7

(1) In a 500 ml autoclave, toluene (60.8 g, 0.66 mole), C$_2$F$_5$C$_2$H$_4$COCF$_3$ (73.2 g, 0.3 mole) and HF (150 g) were charged and reacted at a temperature of 85° to 90° C. while stirring.

After the reaction, the reaction mixture was extracted with trichlorotrifluoroethane. By distilling off trichlorotrifluoroethane from the extract, the compound of the formula:

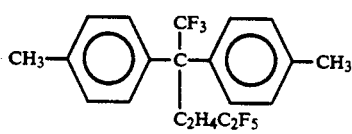

(A-1)

(99.7 g) was obtained as a residue. Yield, 81%.

(2) In a 500 ml autoclave, the compound (A-1) obtained in the above step (1) (82.0 g, 0.20 mole), 60% nitric acid (128 ml) and water (126 ml) were charged and reacted at 180° to 190° C. while stirring. After the reaction, the solid material was recovered by filtration. To the solid material, a 5% aqueous solution of sodium hydroxide (400 ml) was poured to dissolve the material, and the undissolved material was filtered off. The filtrate was acidified with an aqueous solution of sulfuric acid to precipitate a white solid, which was recovered by filtration and dried to obtain the acid of the formula:

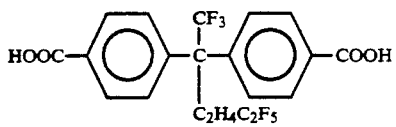

(88.4 g). Yield, 94%.

(3) In a three-necked 2 liter flask, the acid (A2) obtained in the above step (2) (51.7 g, 0.11 mole), conc. nitric acid (176 g) and chloroform (350 ml) were charged. To the mixture, 1.1 N hydrazoic acid (306 ml) was dropwise added at a temperature of 0° to 5° C. After the addition of hydrazoic acid, the mixture was stirred at a temperature of 40° to 45° C. for 2 hours and at room temperature for 12 hours, and then separated into a chloroform layer and an aqueous layer. The aqueous layer was basified with aqueous sodium hydroxide and extracted with chloroform (400 ml). The extract was dried over sodium sulfate, and chloroform was distilled off. The residue was recyrstallized from petroleum benzin/diethyl ether to obtain the amine of the formula:

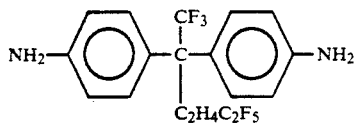

(26.8 g). Yield, 59%.

(4) To a four-necked 500 ml flask, the amine (A-3) obtained in the above step (3) (20.6 g, 0.05 mole) and m-XHF (150 ml) were charged. To the mixture, a solution of maleic anhydride (12.7 g, 0.13 mole) ink m-XHF (150 ml) was dropwise added gradually at 50° C. while stirring. After the addition of maleic anhydride, the mixture was stirred at 50° C. for 30 minutes. Then, to the mixture, BTMAC (0.5 g), Ni(OAc)$_2$.4H$_2$O (0.5 g) and conc. sulfuric acid (1.2 ml) were added and heated under reflux for 10 hours with removing water by a Dean-Stark condenser. An organic phase was neutralized with an aqueous Na$_2$CO$_3$ solution, washed two times with an aqueous NaCl solution and dried over anhydrous Na$_2$SO$_4$. Then, m-XHF was distilled off under reduced pressure to obtain the compound of the formula:

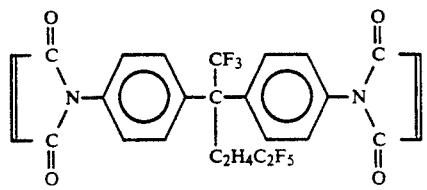

(20.03 g, 0.035 mole). Yield, 70%.

$^1$H-NMR (CDCl$_3$/TMS) δ [ppm]: 1.5–3.0 (broad, 4H), 6.87 (s, 4H), 7.45 (s. 8H).

$^{19}$F-NMR (CDCl$_3$/TFA) δ [ppm]: −12.7 (s, 3F), 2.2 (t, 3F), 47.4 (m, 2F).

IR, γ [cm$^{-1}$]:3500, 1720, 1605, 1515, 1400, 1380, 1190, 1140, 1060, 1015, 1000, 970, 950, 825, 700.

EXAMPLE 8

(1) In a 500 ml autoclave, toluene (60.8 g, 0.66 mole), C$_4$F$_9$C$_2$H$_4$COCH$_3$ (87.0 g, 0.3 mole) and HF (150 g) were charged and reacted at a temperature of 85° to 90° C. while stirring.

After the reaction, the reaction mixture was extracted with trichlorotrifluoroethane. By distilling off trichlorotrifluoroethane from the extract, the compound of the formula:

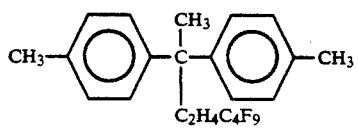

(113.8 g) was obtained as a residue. Yield, 83%.

(2) In a 500 ml autoclave, the compound (B-1) obtained in the above step (1) (91.2 g, 0.20 mole), 60% nitric acid (128 ml) and water (126 ml) were charged and reacted at 180° to 190° C. while stirring. After the reaction, the solid material was recovered by filtration. To the solid material, a 5% aqueous solution of sodium hydroxide (400 ml) was poured to dissolve the material, and the undissolved material was filtered off. The filtrate was acidified with an aqueous solution of sulfuric acid to precipitate a white solid, which was recovered by filtration and dried to obtain the acid of the formula:

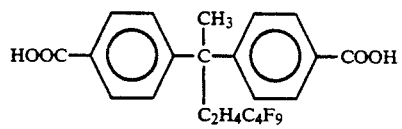

(139.1 g). Yield, 90%.

(3) In a 500 ml atutoclave, the acid (B-2) obtained in the above step (2) (56.76 g, 0.11 mole), conc. nitric acid (176 g) and chloroform (350 ml) were charged. To the mixture, 1.1 N hydrazoic acid (306 ml) was dropwise added at a temperature of 0° to 5° C. After the addition of hydrazoic acid, the mixture was stirred at a temperature of 40° to 45° C. for 2 hours and at room temperature for 12 hours, and then separated into a chloroform layer and an aqueous layer. The aqueous layer was basified with aqueous sodium hydroxide and extracted with chloroform (400 ml). The extract was dried over sodium sulfate, and chloroform was distilled off. The residue was recrystallized from petroleum benzin/diethyl ether to obtain the amine of the formula:

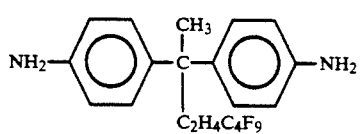

(27.5 g). Yield, 55%.

(4) To a four-necked 500 ml flask, the amine (B-3) obtained in the above step (3) (22.9 g, 0.05 mole) and m-XHF (150 ml) were charged. To the mixture, a solution of maleic anhydride (12.7 g, 0.13 mole) in m-XHF (150 ml) was dropwise added gradually at 50° C. while stirring. After the addition of maleic anhydride, the mixture was stirred at 50° C. for 30 minutes. Then, to the mixture, BTMAC (0.5 g), Ni(OAc)$_2$·4H$_2$O (0.5 g) and conc. sulfuric acid (1.2 ml) were added and heated under reflux for 10 hours with removing water by a Dean-Stark condenser. An organic phase was neutralized with an aqueous Na$_2$CO$_3$ solution, washed two times with an aqueous NaCl solution and dried over anhydrous Na$_2$SO$_4$. Then, m-XHF was distilled off under reduced pressure to obtain the compound of the formula:

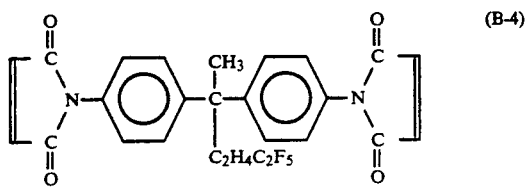

(20.03 g, 0.035 mole). Yield, 70%.

$^1$H-NMR (CDCl$_3$/TMS) δ [ppm]:1.66 (s, 3H), 1.6–3.0 (broad, 4H), 6.86 (s, 4H), 7.46 (s. 8H).

$^{19}$F-NMR (CDCl$_3$/TFA) δ [ppm]:2.3 (t, 3F), 36.7 (m, 2F), 45.8 (m, 2F), 47.5 (t, 2F).

IR, γ [cm$^{-1}$]: 3500, 1720, 1610, 1510, 1400, 1370, 1180, 1145, 1055, 1020, 1000, 970, 950, 830, 705.

EXPERIMENT 1 and Comparative Experiment

A 50% by weight solution of the present fluorine-containing polyimide of Example 1 in NMP was casted on a stainless steel plate and heated for 20 minutes at 80° C., 20 minutes at 150° C. and then one hour at 250° C. to form a cured resin.

The obtained resin was subjected to the following examinations.

In Comparative Experiment, a fluorine-containing polyimide of the formula:

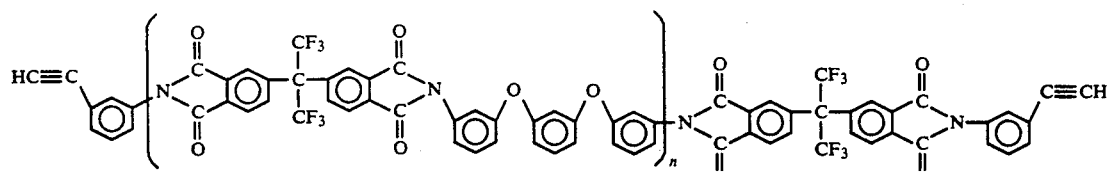

wherein n is 1.0 on an average, was used.

(i) Water absorption

A specimen (76.2 mm×25.4 mm×50 μm) of the cured resin was dried for 24 hours at 50°±3° C., cooled in a desiccator and then weighed (W$_1$). The specimen was immersed in distilled water at 23°±1° C. for 24 hours. Then, after wiping water off, the specimen was weighed (W$_2$). The water absorption (A) of the resin was calculated as follows:

$$A (\%) = \frac{W_2 - W_1}{W_1} \times 100$$

(ii) Refractive index

A refractive index of the cured resin was measured at 23° C. by using an Abbe refractometer.

The results are shown in the following Table 1.

TABLE 1

| Resin | Water absorption | Refractive index ($n_D^{23}$) |
|---|---|---|
| Experiment 1 | 0.25 | 1.468 |
| Comp. Experiment | 1.4 | 1.617 |

It was found that the refractive index of the present compound of Example 1 approximated to that of quartz ($n_D^{23}$ = 1.46).

EXPERIMENT 2

A mixture of the compound (A-4) (9.16 g) and the compound (B-4) (16.07 g) prepared in Example 7 and 8, respectively was dissolved in NMP (30 g) and the obtained solution was casted on a stainless steel plate and heated for 20 minutes at 80° C., 10 minutes at 120° C. 10 minutes at 140° C. and then 2 hours at 190° C. to form a cured resin.

The water absorption of the cured resin was measured in the same manner as in Experiment 1. The cured resin had a water absorption of 0.53%.

What is claimed is:

1. A curable fluorine-containing polyimide of the formula:

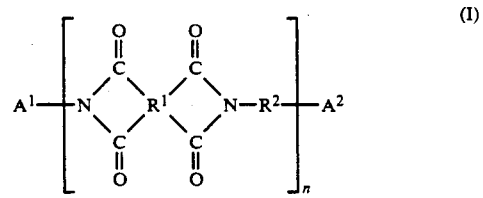

wherein R$^1$ is:

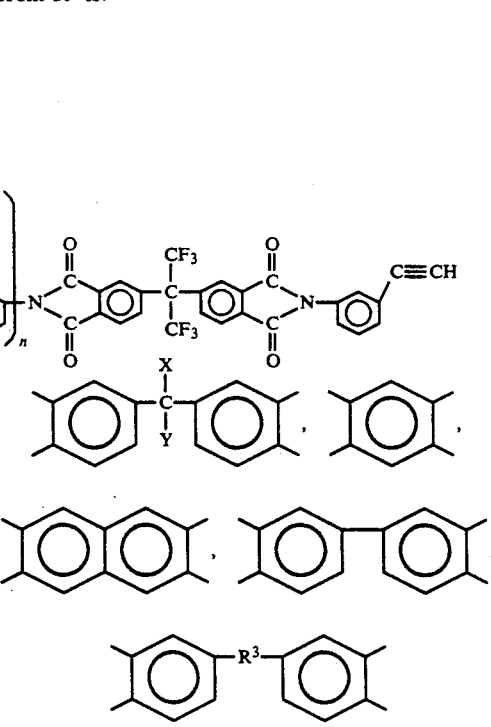

(wherein R$^3$ is —O—, —CO—,

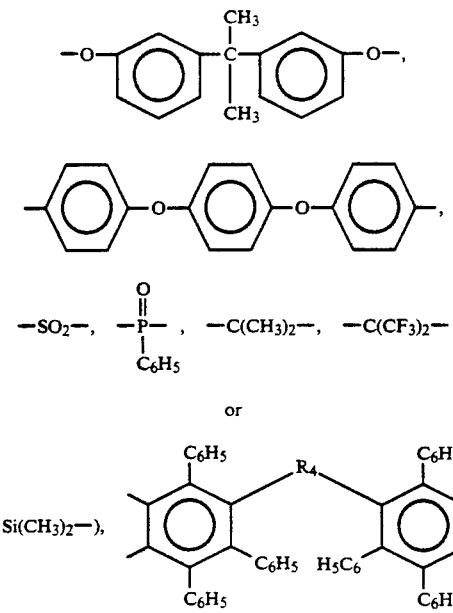
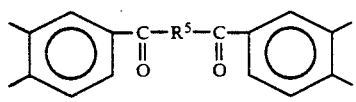
wherein R⁴ is —C₆H₄—, —C₆H₄—O—C₆H₄— or —C₆H₄—O—C₆H₄—O—C₆H₄—) or
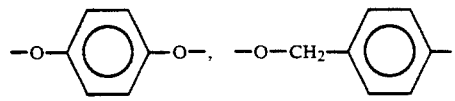
(wherein R⁵ is —O—, —O—(CH₂)₄—O—, —O—(CH₂)₆—O—,
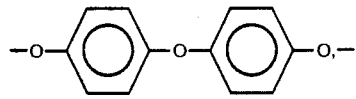
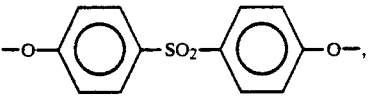
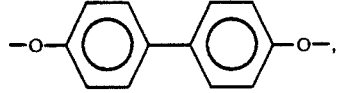
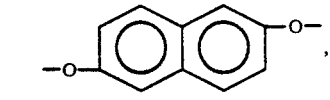
or
-continued
—O—C₂H₄—OOC—⟨C₆H₄⟩—COO—C₂H₄—O—).
R² is
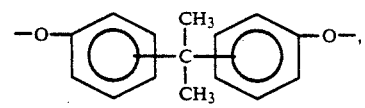
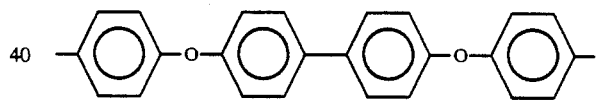
(wherein R⁶ is —O—, —CO—, —S—, —CH₂—, —C(CH₃)₂—, —C(CF₃)₂—, —SO₂—,
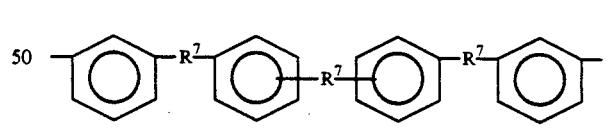
or
—Si(CH₃)₂—)
or
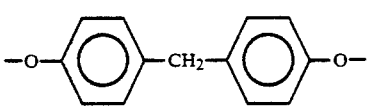
(wherein R⁷ is —O—, —SO₂—, —CH₂, —CO—, —C(CH₃)₂— or —S—),
A¹ is a residue of the formula:
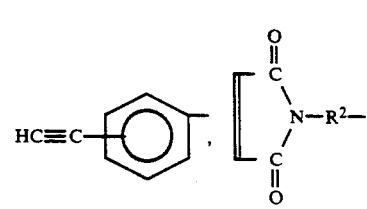
or -continued

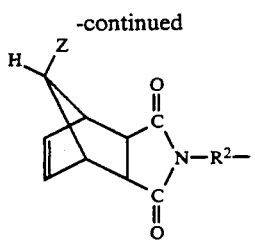

(wherein R² is the same as defined above, and Z is a hydrogen atom or an alkyl group having 1 to 5 carbon atoms), A² is a residue of the formula:

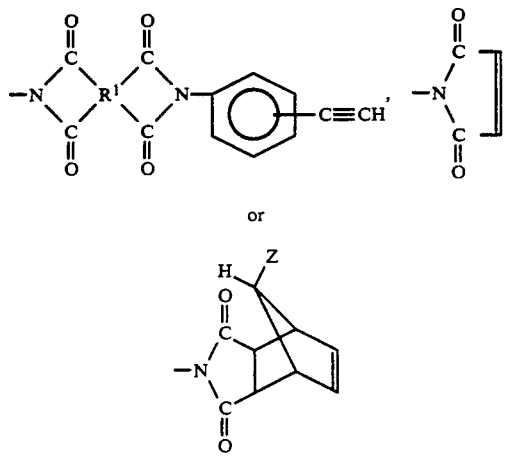

or

(wherein R¹ and Z are the same as defined above), and n is a number of 0 to 90, and at least one of the groups R¹ and R² in the formula (I) contains a substituted methylene group of the formula:

$$-\underset{Y}{\overset{X}{\underset{|}{\overset{|}{C}}}}-$$

(wherein X is a residue of the formula:

wherein Rf is a perfluoroalkyl group having 1 to 10 carbon atoms, R'f is a perfluoroalkyl group having 1 to 12 carbon atoms, p is an integer of 1 to 3, q is an integer of 0 to 3, r is 0 or 1, s is an integer of 0 to 5 and t is an integer of 0 to 5, and Y is the same as X or a hydrogen atom, an alkyl group having 1 to 8 carbon atoms or a fluoroalkyl group having 1 to 8 carbon atoms, provided that, when Y contains no fluorine atom, X contains at least 9 fluorine atoms, or when Y contains at least one fluorine atom, the total number of the fluorine atoms contained in X and Y is at least 8.

2. The polyimide according to claim 1, wherein X in the substituted methylene group is a residue of the formula:

Rf, R'f, r, s and t are the same as defined above.

3. The polyimide according to claim 1, wherein X in the substituted methylene group is a residue of the formula:

wherein Rf, R'f, r, s and t are the same as defined above.

4. The polyimide according to claim 1, wherein X in the substituted methylene group is a residue of the formula:

wherein Rf, R'f, r and s are the same as defined above.

5. The polyimide according to claim 1, wherein X in the substituted methylene group is a residue of the formula:

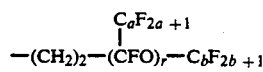

wherein r is the same as defined above, a is an integer of 1 to 8, and b is an integer of 1 to 8.

6. The polyimide according to claim 5, wherein Y in the substituted methylene group is an alkyl group having 1 to 8 carbon atoms or a fluoroalkyl group having 1 to 8 carbon atoms.

7. The polyimide according to claim 5, wherein Y in the substituted methylene group is a fluoroalkyl group having 1 to 8 carbon atoms.

8. The polyimide according to claim 5, wherein Y in the substituted methylene group is a methyl group or a trifluoromethyl group.

9. The polyimide according to claim 5, wherein Y in the substituted methylene group is a trifluoromethyl group.

* * * * *

UNITED STATES PATENT AND TRADEMARK OFFICE
CERTIFICATE OF CORRECTION

PATENT NO. : 5,262,515
DATED : Nov. 16, 1993
INVENTOR(S) : Motonobu KUBO and Tsutomu KOBAYASHI It is certified that error appears in the above-indentified patent and that said Letters Patent is hereby corrected as shown below:

Title Page
Item (30) Line 2, change "63-144288" to --63-144388--

Signed and Sealed this

Seventeenth Day of May, 1994

Attest:

BRUCE LEHMAN

*Attesting Officer*  *Commissioner of Patents and Trademarks*